United States Patent
Choi et al.

(10) Patent No.: US 10,426,599 B2
(45) Date of Patent: Oct. 1, 2019

(54) MULTIFOCAL LENS HAVING REDUCED CHROMATIC ABERRATIONS

(71) Applicant: Novartis AG, Basel (CH)

(72) Inventors: Myoung-Taek Choi, Arlington, TX (US); Xin Hong, Fort Worth, TX (US); Yueai Liu, Arlington, TX (US)

(73) Assignee: Novartis AG, Basel (CH)

(*) Notice: Subject to any disclaimer, the term of this patent is extended or adjusted under 35 U.S.C. 154(b) by 91 days.

(21) Appl. No.: 15/363,398

(22) Filed: Nov. 29, 2016

(65) Prior Publication Data

US 2018/0147050 A1     May 31, 2018

(51) Int. Cl.
*A61F 2/16*     (2006.01)
*G02B 27/58*     (2006.01)
*G02C 7/02*     (2006.01)
*G02C 7/04*     (2006.01)
*G02C 7/06*     (2006.01)

(52) U.S. Cl.
CPC .......... *A61F 2/1618* (2013.01); *A61F 2/1654* (2013.01); *G02B 27/58* (2013.01); *G02C 7/024* (2013.01); *G02C 7/041* (2013.01); *G02C 7/042* (2013.01); *G02C 7/06* (2013.01); *A61F 2/1656* (2013.01); *G02C 2202/20* (2013.01); *G02C 2202/22* (2013.01)

(58) Field of Classification Search
CPC ..... A61F 2/1618; A61F 2/1654; G02B 27/58; G02C 7/024; G02C 7/041; G02C 7/042; G02C 7/06
USPC .................................................... 351/159.43
See application file for complete search history.

(56) References Cited

U.S. PATENT DOCUMENTS

| | | | |
|---|---|---|---|
| 4,210,391 A | 7/1980 | Cohen | |
| 4,637,697 A | 1/1987 | Freeman | |
| 4,881,805 A * | 11/1989 | Cohen | G02B 5/1876 351/159.42 |
| 4,995,715 A * | 2/1991 | Cohen | G02B 5/1876 351/159.44 |
| 5,054,905 A * | 10/1991 | Cohen | G02B 5/1876 351/159.42 |
| 5,121,980 A * | 6/1992 | Cohen | G02B 5/1876 351/159.41 |
| 2006/0098162 A1 | 5/2006 | Bandhauer et al. | |
| 2006/0098163 A1 * | 5/2006 | Bandhauer | A61F 2/1613 351/159.41 |
| 2006/0244905 A1 * | 11/2006 | Piers | A61B 3/0025 351/159.05 |
| 2008/0198326 A1 * | 8/2008 | Piers | A61B 3/0025 351/159.79 |
| 2009/0234448 A1 * | 9/2009 | Weeber | A61F 2/1613 623/6.3 |
| 2010/0312337 A1 * | 12/2010 | Zhang | A61F 2/1613 623/6.31 |
| 2011/0098811 A1 | 4/2011 | Hong et al. | |

(Continued)

*Primary Examiner* — James R Greece
(74) *Attorney, Agent, or Firm* — Baker Botts L.L.P.

(57) ABSTRACT

A method and system provide a multifocal ophthalmic device. The ophthalmic lens has an anterior surface, a posterior surface and at least one diffractive structure including a plurality of echelettes. The echelettes have at least one step height of at least one wavelength and not more than two wavelengths in optical path length. The diffractive structure(s) reside on at least one of the anterior surface and the posterior surface. The diffractive structure(s) provide a plurality of focal lengths for the ophthalmic lens.

10 Claims, 5 Drawing Sheets

(56) References Cited

U.S. PATENT DOCUMENTS

| | | | |
|---|---|---|---|
| 2011/0149236 A1* | 6/2011 | Weeber | A61F 2/1618 351/159.01 |
| 2014/0118684 A1 | 5/2014 | Piers et al. | |
| 2014/0168602 A1* | 6/2014 | Weeber | A61F 2/1637 351/159.44 |
| 2015/0320547 A1* | 11/2015 | Rosen | A61F 2/1613 623/6.23 |
| 2016/0320633 A1 | 11/2016 | Weeber | |

* cited by examiner

US 10,426,599 B2

MULTIFOCAL LENS HAVING REDUCED CHROMATIC ABERRATIONS

FIELD

The present disclosure relates generally to ophthalmic lenses and more particularly to multifocal ophthalmic lenses having reduced chromatic aberrations.

BACKGROUND

Intraocular lenses (IOLs) are implanted in patients' eyes either to replace a patient's lens or to complement the patient's lens. The IOL may be implanted in place of the patient's lens during cataract surgery. Alternatively, an IOL may be implanted in a patient's eye to augment the optical power of the patient's own lens.

Some conventional IOLs are single focal length IOLs, while others are multifocal IOLs. Single focal length IOLs have a single focal length or single power. Objects at the focal length from the eye/IOL are in focus, while objects nearer or further away may be out of focus. Although objects are in perfect focus only at the focal length, objects within the depth of field (within a particular distance of the focal length) are still acceptably in focus for the patient to consider the objects in focus. Multifocal IOLs, on the other hand, have at least two focal lengths. For example, a bifocal IOL has two focal lengths for improving focus in two ranges: a far focus corresponding to a larger focal length and a near focus corresponding to a smaller focal length. Thus, a patient's distance vision and near vision may be improved. A conventional diffractive bifocal IOL typically uses the $0^{th}$ diffractive order for distance focus/vision and the $1^{st}$ diffraction order for near focus/vision. Trifocal IOLs have three foci: a far focus for distance vision, a near focus for near vision and an intermediate focus for intermediate vision that has an intermediate focal length between that of the near and far focuses. A conventional diffractive trifocal IOL typically uses the $0^{th}$ diffractive order for distance vision, the $1^{st}$ diffractive order for intermediate vision and the $2^{nd}$ diffraction order for near vision. Multifocal IOLs may improve the patient's ability to focus on distant and nearby objects. Stated differently, the depth of focus for the patient may be enhanced.

Although multifocal lenses may be used to address conditions such as presbyopia, there are drawbacks. Multifocal IOLs may also suffer from longitudinal chromatic aberration. Different colors of light have different wavelengths and, therefore, different foci. As a result, the multifocal IOL focuses light of different colors at different distances from the lens. The multifocal IOL may be unable to focus light of different colors at the patient's retina. The polychromatic image contrast for the multifocal IOL, particularly for distance vision, may be adversely affected.

Accordingly, what is needed is a system and method for addressing chromatic aberration in multifocal IOLs.

SUMMARY

A method and system provide a multifocal ophthalmic device. The ophthalmic lens has an anterior surface, a posterior surface and at least one diffractive structure including a plurality of echelettes. The echelettes have at least one step height of at least one wavelength and not more than two wavelengths in optical path length. The diffractive structure(s) reside on at least one of the anterior surface and the posterior surface. The diffractive structure(s) provide a plurality of focal lengths for the ophthalmic lens.

The multifocal lens may have the diffractive structure(s) described above may have reduced chromatic aberration. As a result, image quality may be improved.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION

The exemplary embodiments relate to ophthalmic devices such as IOLs and contact lenses. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. For example, the method and system are described primarily in terms of IOLs. However, the method and system may be used with contact lenses and spectacle lenses. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

A method and system provide a multifocal ophthalmic device. The ophthalmic device includes an ophthalmic lens configured for use based upon a wavelength. The ophthalmic lens has an anterior surface, a posterior surface and at least one diffractive structure including a plurality of echelettes. The echelettes have at least one step height of at least one wavelength and not more than two wavelengths in optical path length. The diffractive structure(s) reside on at least one of the anterior surface and the posterior surface. The diffractive structure(s) provide a plurality of focal lengths for the ophthalmic lens.

Figure 1A:
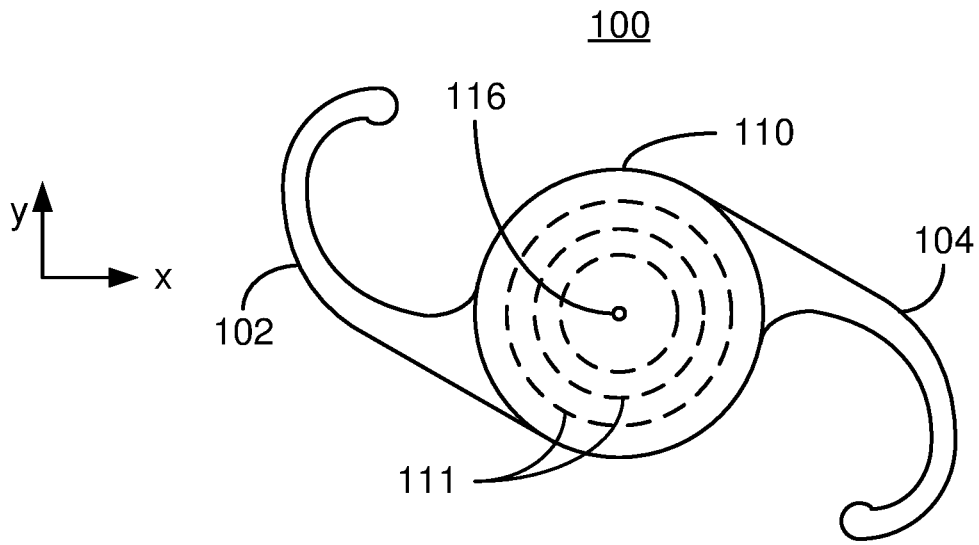
FIGS. 1A and 1B depict a plan and side views of an exemplary embodiment of a multifocal ophthalmic device that may have reduced chromatic aberration.
Figure 1B:
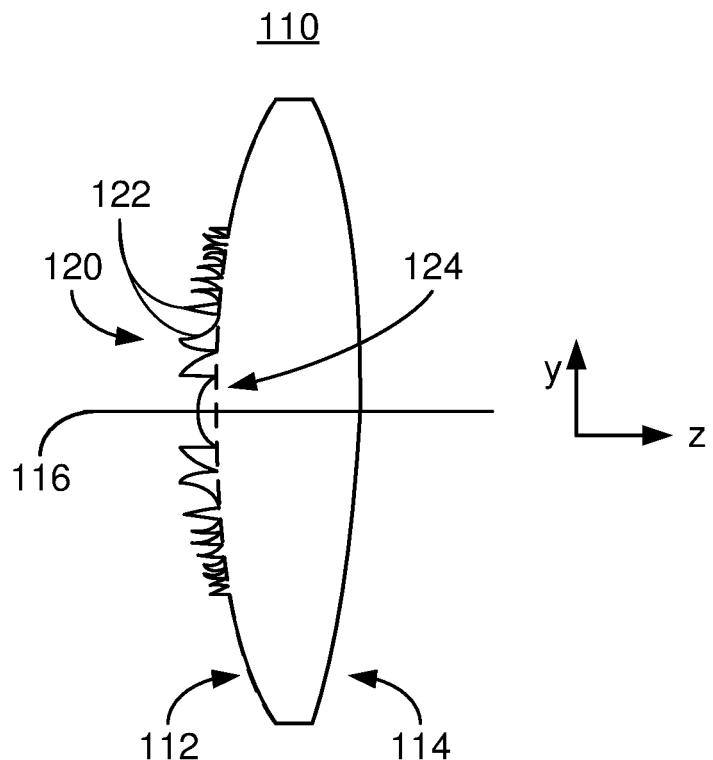

FIGS. 1A-1B depict an exemplary embodiment of an ophthalmic device 100 that may be used as an IOL. FIG. 1A depicts a plan view of the ophthalmic device 100, while FIG. 1B depicts a side view of the ophthalmic lens 110. For clarity, FIGS. 1A and 1B are not to scale and only some features are shown. The ophthalmic device 100 includes an ophthalmic lens 110 (herein after "lens") as well as haptics 102 and 104. The lens 110 may be made of a variety of optical materials including but not limited to one or more of silicone, a hydrogel, an acrylic and AcrySof®. Haptics 102 and 104 are used to hold the ophthalmic device 100 in place in a patient's eye (not explicitly shown). However, in other embodiments, other mechanism(s) might be used to retain the ophthalmic device in position in the eye. Thus, the haptics 102 and/or 104 might be omitted. For clarity, the haptics are not depicted in the remaining drawings. Although the lens 110 is depicted as having a circular cross section in the plan view of FIG. 1, in other embodiments, other shapes may be used. Further, although described in the context of an IOL, the lens 110 may be a contact lens. In such a case, the haptics 102 would be omitted and the lens 110 sized and otherwise configured to reside on the surface of the eye.

The lens 110 is a multifocal lens. The lens 110 has an anterior surface 112 a posterior surface 114 and an optic axis 116. The lens is also characterized by a diffractive structure 120 and a base curvature 124. The lens 110 may be determined provide a base power, astigmatism correction and/or other vision correction(s). The lens 110 may be aspheric, toroidal and/or biconic, have the same or different base curvatures on the surfaces 112 and 114 and/or other characteristics that are not shown or discussed in detail for simplicity. Although one diffractive structure 120 is shown on the anterior surface 112, the diffractive structure 120 might be located on the posterior surface 114. In still other embodiments, diffractive structures may be located on the anterior surface 112 and the posterior surface 114. Such diffractive structures may be the same or different. The diffractive structure 120 may, but need not, be partial aperture diffractive structure. In such embodiments, a refractive power compensator may be incorporated into the base curvature 124 in the diffractive zone to neutralize the base diffractive power.

The lens 110 may have zones 111 corresponding to different ranges in distance perpendicular to the optic axis 116 (i.e. different radii). A zone 111 is a circle or an annular ring along the surface from a minimum radius to a maximum radius from the optic axis 116. The diffractive structure 120 and/or the base curvature 124 may be different in different zones. For example, in some embodiments, the diffractive structure 120 may have ring diameters for the zones set by the Fresnel diffractive lens criteria. Alternatively, other criteria may be used. In other embodiments, one or both of these features may not change between zones. For example, the base curvature may be consistent across the anterior surface 112, while the diffractive structure 120 changes for different zones 111. The diffractive structure 120 may use different diffractive orders to create multiple focuses, as described below.

The diffractive structure 120 provides multiple focal lengths. In some embodiments, for example, the diffractive structure 120 is used to provide a bifocal (two focal lengths for near and distance vision) lens 110. In other embodiments, the diffractive structure 120 may provide a trifocal (three focal lengths for near, intermediate and distance vision) lens 110. A quadrifocal or other multifocal lens might also be provided. The diffractive structure 120 is configured for particular wavelength(s). For example, different zones 111 of the diffractive structure 120 may be configured for light of different wavelengths. Alternatively, the diffractive structure 120 may be designed for light of a single wavelength. Without more, such a structure would suffer from chromatic aberration.

The diffractive structure 120 includes and is formed of steps termed echelettes 122. As can be seen in FIG. 1B, the physical height of the echelettes 122 may vary. In other embodiments, the physical height of the echelettes 122 may be constant. The spacing between the echelettes 122 and other characteristics of the echelettes 122 may also stay the same or vary across the lens 110. The optical step height of the echelettes 122 is the physical height (shown in FIG. 1B) multiplied by the difference between the index of refraction of the lens 110 and the index of refraction of the surrounding media in which the lens 110 is to be used.

The optical step height(s) of the echelettes 122 may be not less than the wavelength of light and not more than twice the wavelength of light. In other words, $\lambda \leq \Delta n \cdot h \leq 2\lambda$, where h is the physical height of the echelette 122, $\lambda$ is the wavelength of light for which the appropriate region of the diffractive structure 120 is configured and $\Delta n$ is the difference in the index of refraction described above. In some embodiments, $\lambda < \Delta n \cdot h < 2\lambda$. The echelettes 122 may also be apodized (have a decreased step height). However, the minimum step height for such apodized echelettes 122 is still $\lambda$. Utilizing a step height in this range excludes the zeroth ($0^{th}$) diffractive order from use in the lens 110.

In some embodiments, for example, the diffractive structure 120 is used to provide a bifocal (two focal lengths for near and distance vision) lens 110. A bifocal lens 110 may utilize the first ($1^{st}$) diffractive order and the second ($2^{nd}$) diffractive order. In some embodiments, the $1^{st}$ diffractive order is utilized for distance vision, while the $2^{nd}$ diffractive order is used for near vision. In other embodiments, the diffractive structure 120 may provide a trifocal (three focal lengths for near, intermediate and distance vision) lens 110. A trifocal lens 110 may utilize the $1^{st}$ diffractive order, the $2^{nd}$ diffractive order and the third ($3^{rd}$) diffractive order. In some embodiments, the $1^{st}$ diffractive order is used for distance vision, the $2^{nd}$ diffractive order is used for intermediate vision and the $3^{rd}$ diffractive order is used for near vision. In other embodiments, the diffractive structure 120 is configured for a quadrifocal lens 110. Such a quadrifocal lens 110 may utilize the $1^{st}$ diffractive order, the $2^{nd}$ diffractive order, the $3^{rd}$ diffractive order and the fourth ($4^{th}$) diffractive order. In some embodiments, the $1^{st}$ diffractive order is used for distance vision, the $2^{nd}$ diffractive order may be empty, the $3^{rd}$ diffractive order is used for intermediate vision and the $4^{th}$ diffractive order is used for near vision. In other embodiments, the $1^{st}$ diffractive order is used for distance vision, the $2^{nd}$ diffractive order may be used for intermediate vision, the $3^{rd}$ diffractive order may be empty and the $4^{th}$ diffractive order is used for near vision. In other embodiments, different diffractive orders may be used for different focal ranges. However, the $0^{th}$ order is excluded.

The lens 110 may have improved performance while maintaining the benefits of a multifocal lens. Because the lens 110 is a multifocal lens, the ophthalmic device 100 may be used to treat conditions such as presbyopia. Other conditions may be treated and performance of the lens 110 may be improved through the use of the base curvature 124, asphericity of the lens 110, toricity of the lens 110, apodization of the echelettes 122 and other characteristics of the lens. In addition, the lens 110 may have reduced chromatic aberration. Configuration of the echelettes 122 to exclude the $0^{th}$ diffractive order (e.g. have a step height that is at least equal to the wavelength and not more than twice the wavelength of light) may reduce the longitudinal chromatic aberration. In some embodiments, the chromatic aberration may be significantly reduced. Consequently, polychromatic or white light image contrast may be improved for distance, near, and/or intermediate vision for multifocal lenses 110. Performance of the lens 110 and ophthalmic device 100 may thus be enhanced.

Figure 2:
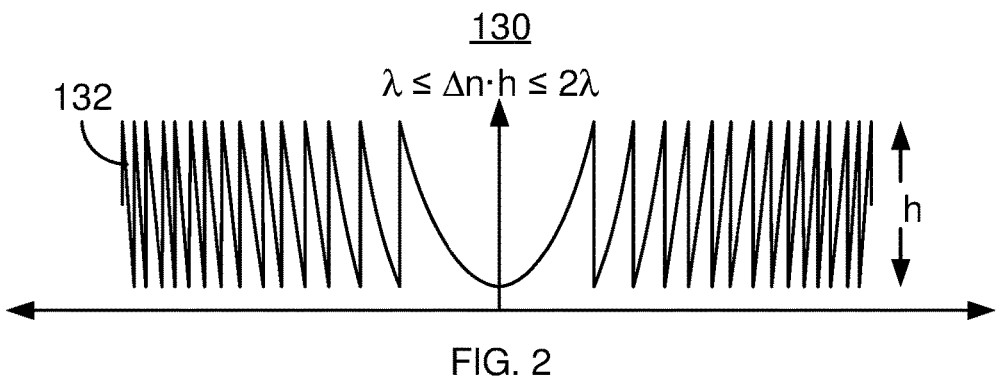
FIG. 2 depicts a side view of an exemplary embodiment of a diffractive structure for a bifocal lens of an ophthalmic device that may have reduced chromatic aberration.
Figure 3A:
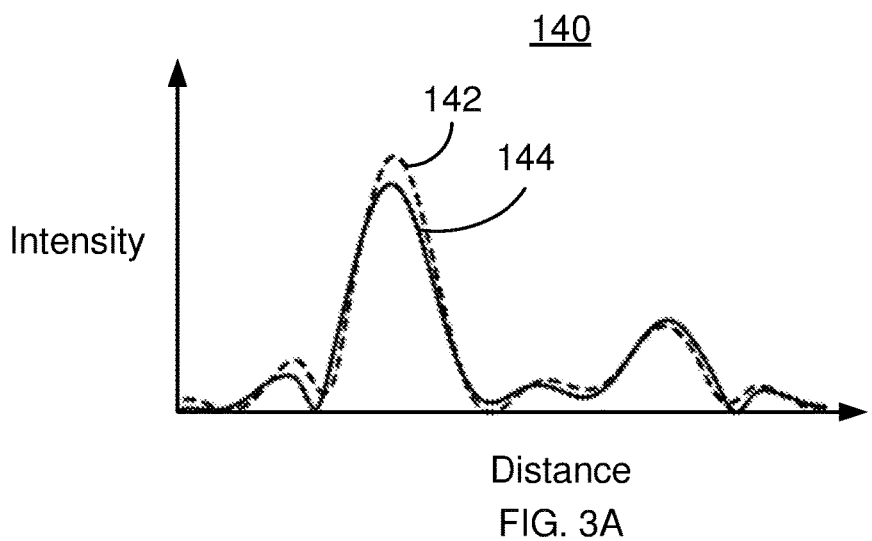
FIGS. 3A-3B depict exemplary embodiments of the intensity versus distance for a bifocal lens that may have reduced chromatic aberration and for a lens made without accounting for chromatic aberration reduction.
Figure 3B:
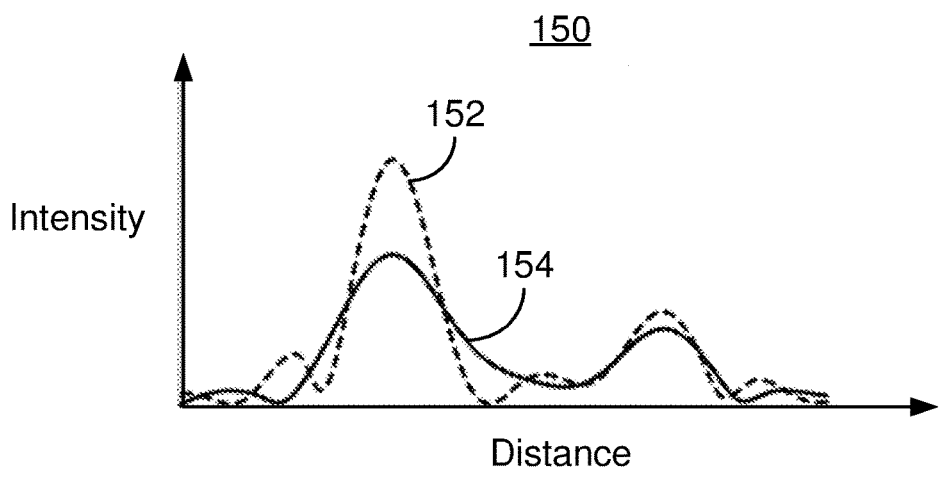

The benefits of the ophthalmic lens 110 may be better understood with respect specific bifocal, trifocal and quadrifocal embodiments. FIG. 2 depicts a side view of another exemplary embodiment of a diffractive structure 130 that may be used in a bifocal diffractive lens 110. FIGS. 3A and 3B are graphs 140 and 150, respectively, depicting exemplary embodiments of the intensity versus distance for a reduced chromatic aberration bifocal lens 110 made with the diffractive structure 130 and for a bifocal diffractive lens made without accounting for chromatic aberration reduction. Referring to FIGS. 2-3B, the diffractive structure 130 may take the place of the diffractive structure 120. The diffractive structure 130 is shown with the base curvature removed. FIGS. 2-3B are not to scale and for explanatory purposes only.

The diffractive structure 130 has echelettes 132 having a single physical height, h. This physical height corresponds to a single step height for the lens 110. As indicated in FIG. 2, the step height is not less than the wavelength for which the diffractive structure 130 is configured and not more than twice the wavelength for which the diffractive structure 130 is configured ($\lambda \leq \Delta n \cdot h \leq 2\lambda$). In some embodiments, $\lambda < \Delta n \cdot h < 2\lambda$. The diffractive structure 130 thus omits the $0^{th}$ order.

FIG. 3A is a graph 140 depicting the intensity versus distance for two wavelengths for a bifocal lens using the diffractive structure 130. The intensity versus distance for green light is shown by dashed curve 142, while the intensity versus distance for polychromatic light is shown by curve 144. FIG. 3B is a graph 150 depicting the intensity versus distance for two wavelengths for a bifocal lens that does not account for chromatic aberration reduction. The intensity versus distance for green light is shown by dashed curve 152, while the intensity versus distance for polychromatic light is shown by curve 154. As can be seen by a comparison between graphs 140 and 150, the peaks for the curves 142 and 144 match significantly more closely than the peaks for the curves 152 and 154. The diffractive structure 130 focuses light having different wavelengths at distances that are closer to being the same. Thus, chromatic aberration has been reduced for the diffractive structure 130.

Figure 4:
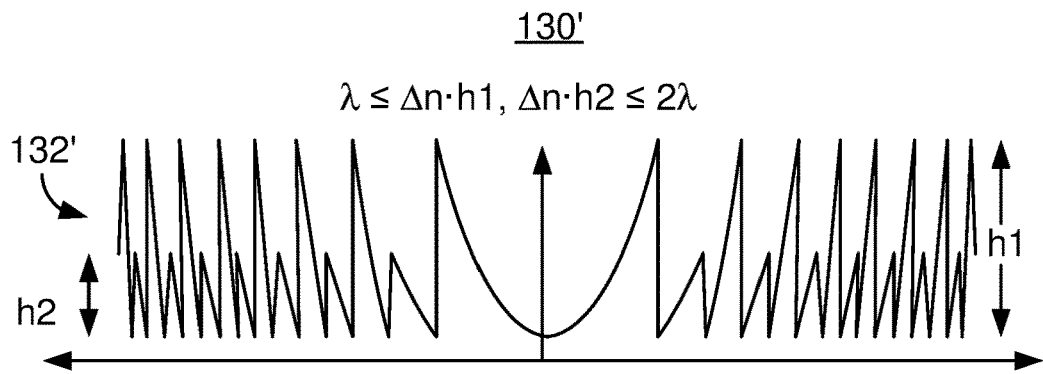
FIG. 4 depicts a side view of an exemplary embodiment of a diffractive structure for a trifocal lens of an ophthalmic device that may have reduced chromatic aberration.
Figure 5A:
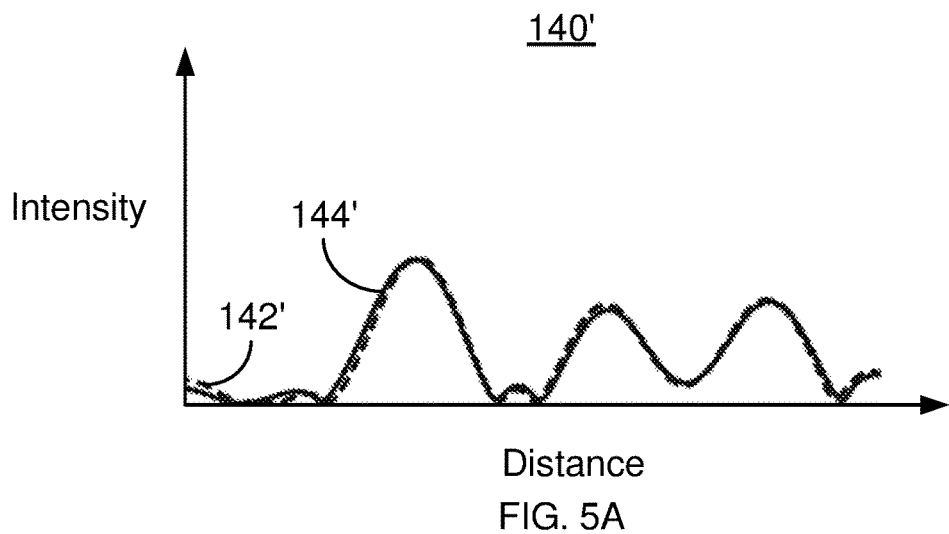
FIGS. 5A-5B depict exemplary embodiments of the intensity versus distance for a trifocal lens that may have reduced chromatic aberration and for a lens made without accounting for chromatic aberration reduction.
Figure 5B:
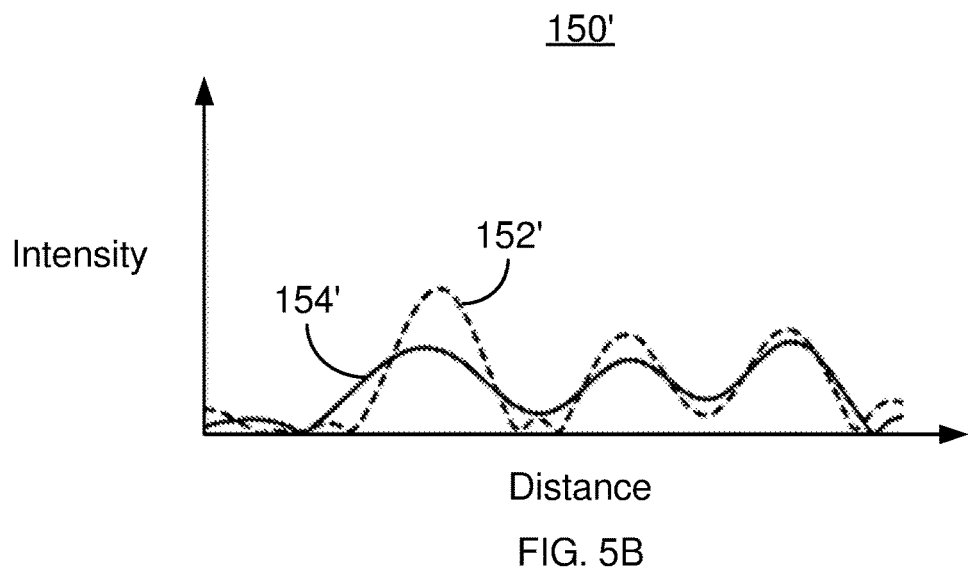

FIG. 4 depicts a side view of another exemplary embodiment of a diffractive structure 130' that may be used in a trifocal diffractive lens 110. FIGS. 5A and 5B are graphs 140' and 150', respectively, depicting exemplary embodiments of the intensity versus distance for a reduced chromatic aberration trifocal lens 110 made with the diffractive structure 130' and for a trifocal diffractive lens made without accounting for chromatic aberration reduction. The diffractive structure 130' thus omits the $0^{th}$ order. Referring to FIGS. 4-5B, the diffractive structure 130' may take the place of the diffractive structure 120. The diffractive structure 130' is shown with the base curvature removed. FIGS. 4-5B are not to scale and for explanatory purposes only.

The diffractive structure 130' has echelettes 132' having a two different physical heights, h1 and h2. These physical heights correspond to two step heights for the lens 110 (h1≠h2). As indicated in FIG. 4, the step heights are not less than the wavelength for which the diffractive structure 130' is configured and not more than twice the wavelength for which the diffractive structure 130 is configured ($\lambda \leq \Delta n \cdot h1 \leq 2\lambda$ and $\lambda \leq \Delta n \cdot h2 \leq 2\lambda$). In some embodiments, $\lambda < \Delta n \cdot h1 < 2\lambda$ and $\lambda < \Delta n \cdot h2 < 2\lambda$. The diffractive structure 130' thus omits the $0^{th}$ order.

FIG. 5A is a graph 140' depicting the intensity versus distance for green light in dashed curve 142' and polychromatic light in curve 144' for a trifocal lens using the diffractive structure 130'. FIG. 3B is a graph 150' depicting the intensity versus distance for green light in dashed 152' and polychromatic light in curve 154' for a trifocal lens that does not account for chromatic aberration reduction. As can be seen by a comparison between graphs 140' and 150', the peaks for the curves 142' and 144' match significantly better than the peaks for the curves 152' and 154'. Light having different wavelengths are thus focused at distances that are closer to being the same. Thus, chromatic aberration has been reduced for the diffractive structure 130'.

Figure 6:
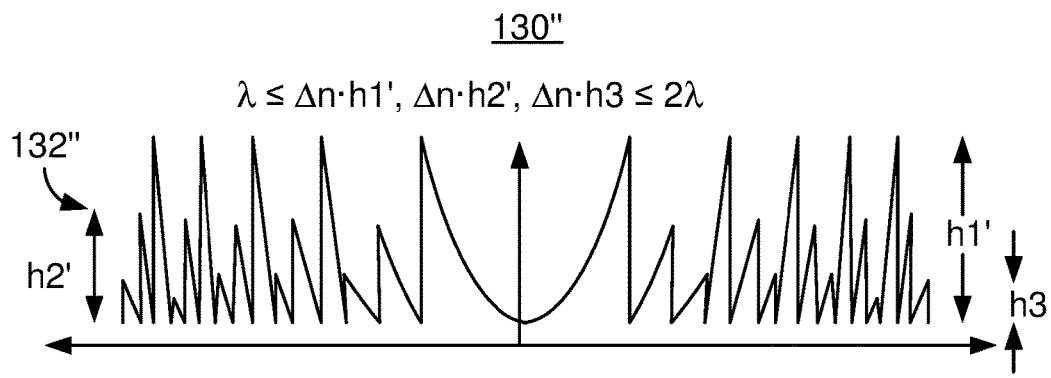
FIG. 6 depicts a side view of an exemplary embodiment of a diffractive structure for a quadrifocal lens of an ophthalmic device that may have reduced chromatic aberration.
Figure 7A:
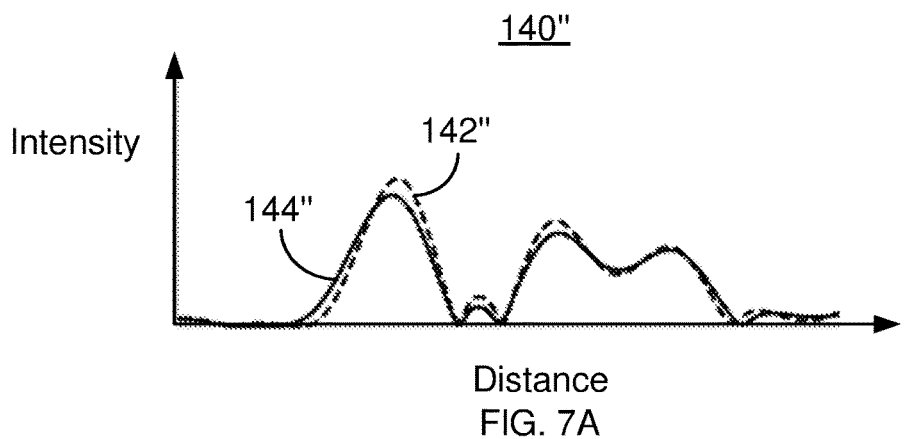
FIGS. 7A-7B depict exemplary embodiments of the intensity versus distance for a quadrifocal lens that may have reduced chromatic aberration and for a lens made without accounting for chromatic aberration reduction.
Figure 7B:
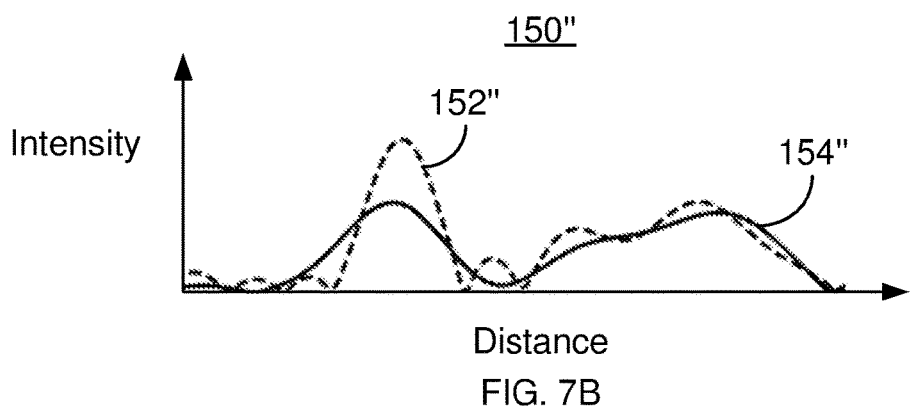

FIG. 6 depicts a side view of another exemplary embodiment of a diffractive structure 130" that may be used in a quadrifocal diffractive lens 110. FIGS. 7A and 7B are graphs 140" and 150", respectively, depicting exemplary embodiments of the intensity versus distance for a reduced chromatic aberration quadrifocal lens 110 made with the diffractive structure 130" and for a quadrifocal diffractive lens made without accounting for chromatic aberration reduction. Referring to FIGS. 6-7B, the diffractive structure 130" may take the place of the diffractive structure 120. The diffractive structure 130" is shown with the base curvature removed. FIGS. 6-7B are not to scale and for explanatory purposes only.

The diffractive structure 130" has echelettes 132" having a three different physical heights, h1', h2' and h3. These physical heights correspond to three different step heights for the lens 110 (h1'≠h2', h1'≠h3, h2'≠h3). As indicated in FIG. 6, the step heights are not less than the wavelength for which the diffractive structure 130" is configured and not more than twice the wavelength for which the diffractive structure 130 is configured ($\lambda \leq \Delta n \cdot h1' \leq 2\lambda$, $\lambda \leq \Delta n \cdot h2' \leq 2\lambda$ and $\lambda \leq \Delta n \cdot h3 \leq 2\lambda$). In some embodiments, $\lambda < \Delta n \cdot h1' < 2\lambda$, $\lambda < \Delta n \cdot h2' < 2\lambda$ and $\lambda < \Delta n \cdot h3 < 2\lambda$. The diffractive structure 130" thus omits the $0^{th}$ order.

FIG. 7A is a graph 140" depicting the intensity versus distance for green light in dashed 142" and polychromatic light in curve 144" for a quadrifocal lens using the diffractive structure 130". FIG. 7B is a graph 150" depicting the intensity versus distance for green light in dashed curve 152" and polychromatic light in curve 154" for a quadrifocal lens that does not account for chromatic aberration reduction. As can be seen by a comparison between graphs 140" and 150", the peaks for the curves 142" and 144" match more closely than the peaks for the curves 152" and 154". The diffractive structure 130" thus focuses light having different wavelengths at distances that are closer to being the same. Thus, chromatic aberration has been reduced for the diffractive structure 130".

A bifocal, trifocal and/or quadrifocal lens using the diffractive structures 130, 130' and/or 130" may have improved performance. Such a lens may have multiple focal lengths as well as other characteristics that can improve treatment of the patient's vision and reduce visual artifact. In addition, configuration of the echelettes 132, 132' and/or 132" to exclude the $0^{th}$ diffractive order (e.g. have a step height that is at least equal to the wavelength and not more than twice the wavelength of light) may reduce the longitudinal chromatic aberration. In some embodiments, the chromatic aberration may be significantly reduced. Consequently, polychromatic or white light image contrast may be improved for distance, near, and/or intermediate vision for the diffractive structures 130, 130' and/or 130". Performance of a lens and ophthalmic device made using the diffractive structures 130, 130' and/or 130" may thus be enhanced.

Figure 8:
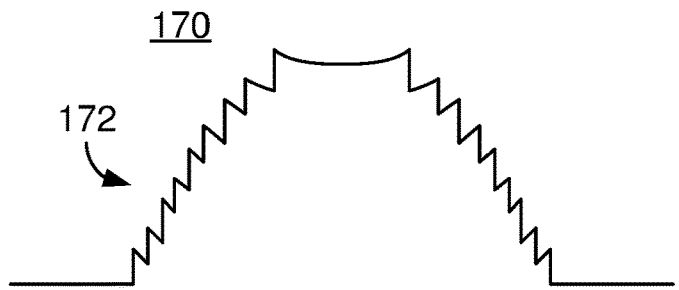
FIG. 8 depicts a side view of another exemplary embodiment of a multifocal diffractive lens of an ophthalmic device that may have reduced chromatic aberration.

FIG. 8 depicts a side view of a portion of another exemplary embodiment of a lens 170 that may have reduced chromatic aberration. FIG. 8 is not to scale and for explanatory purposes only. The lens 170 has a diffractive structure 172 that is a partial aperture diffractive structure. In such embodiments, a refractive power compensator may be incorporated into the base curvature in the diffractive zone to neutralize the base diffractive power. The diffractive structure 172 has echelettes having a single different physical height. In other embodiments, multiple physical heights may be used. The physical height(s) correspond to step height(s) for the lens. The step heights are not less than the wavelength for which the diffractive structure 170 is configured and not more than twice the wavelength for which the diffractive structure 170 is configured. The partial aperture diffractive structure 170 thus omits the $0^{th}$ order. Thus, the lens 170 may have improved performance as described above.

Figure 9:
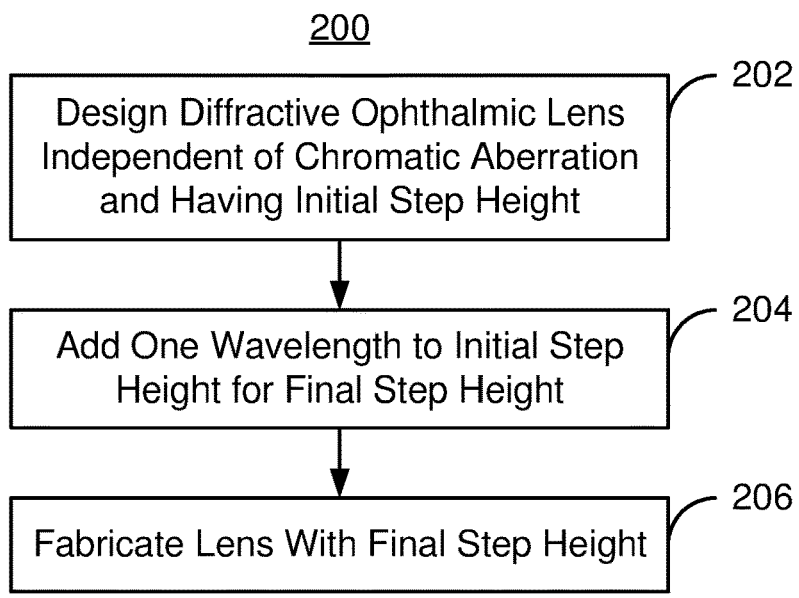
FIG. 9 is flow chart depicting an exemplary embodiment of a method for fabricating an ophthalmic device that may have reduced chromatic aberration.

FIG. 9 is an exemplary embodiment of a method 200 for providing a multifocal diffractive lens having reduced chromatic aberration. For simplicity, some steps may be omitted, interleaved, and/or combined. The method 200 is also described in the context the ophthalmic device 100 and lens 110 and diffractive structure 120. However, the method 200 may be used with one or more other diffractive structure 130' and/or 130" and/or an analogous ophthalmic device.

The diffractive structure for the lens 110 and that does not account for chromatic aberration reduction is designed, via step 202. Step 202 may include defining the zone size and characteristics, the initial step height(s) of the echelettes and other features of the diffractive structure. This generally results in a diffractive structure that has a step height that is less than the wavelength.

A particular amount is added to the step height for each of the echelettes, via step 204. Step 204 generally includes adding a wavelength to each step height. Regardless of the amount added, the resultant, final step height is at least one wavelength and not more than two wavelengths. Alternatively, step 204 may include another mechanism for removing the zeroth diffractive order from the diffractive structure. Thus, the step height for the diffractive structure 120 is determined.

The lens(es) 110 are fabricated, via step 206. Thus, the desired diffractive structure 120 having a step height that is at least as large as the wavelength and not more than twice the wavelength may be provided. The diffractive structure(s) 130, 130', 130" and/or an analogous diffractive structure may be provided and the benefits thereof achieved.

Figure 10:
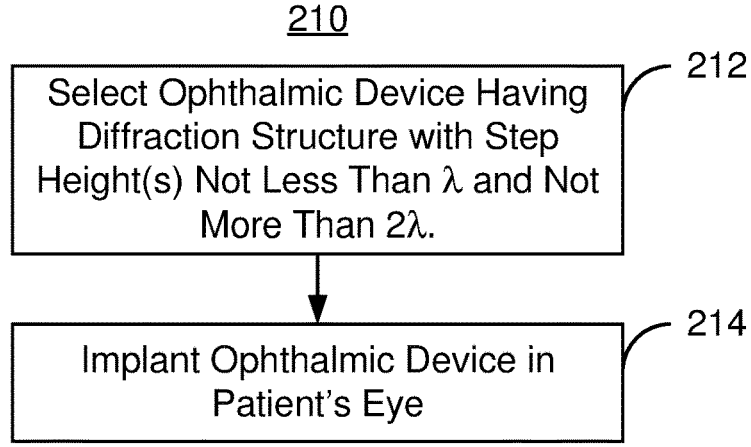
FIG. 10 is flow chart depicting an exemplary embodiment of a method for utilizing an ophthalmic device including a multifocal lens that may have reduced chromatic aberration.

FIG. 10 is an exemplary embodiment of a method 210 for treating an ophthalmic condition in a patient. For simplicity, some steps may be omitted, interleaved, and/or combined. The method 210 is also described in the context of using the ophthalmic device 100 and ophthalmic lens 110. However, the method 210 may be used with one or more of diffractive structures 130, 130', 130" and/or an analogous diffractive structure.

An ophthalmic device 100 for implantation in an eye of the patient is selected, via step 212. The ophthalmic device 100 includes an ophthalmic lens 110 having a diffractive structure 120 that has reduced chromatic aberration. A lens having a diffractive structure 120, 130, 130', 130" and/or an analogous diffractive structure may thus be selected for use.

The ophthalmic device 100 is implanted in the patient's eye, via step 204. Step 204 may include replacing the patient's own lens with the ophthalmic device 100 or augmenting the patient's lens with the ophthalmic device. Treatment of the patient may then be completed. In some embodiments implantation in the patient's other eye of another analogous ophthalmic device may be carried out.

Using the method 200, the diffractive structure 120, 130, 130', 130" and/or analogous diffractive structure may be used. Thus, the benefits of one or more of the ophthalmic lenses 110, 110', 110", and/or 110''' may be achieved.

A method and system for providing an ophthalmic device have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

We claim:

1. A multifocal ophthalmic lens comprising:
   an anterior surface;
   a posterior surface; and
   at least one diffractive structure including a plurality of echelettes having at least three different step heights of at least one wavelength and not more than two wavelengths in optical path length, the at least one diffractive structure residing on at least one of the anterior surface and the posterior surface, the at least one diffractive structure providing:
   a first diffractive order for a first focus corresponding to a first focal length;
   a second diffractive order for a second focus corresponding to a second focal length, the second focal length being different from the first focal length;
   a third diffractive order for a third focus corresponding to a third focal length, the third focal length being different from the first focal length and the second focal length;
   a fourth diffractive order for a fourth focus corresponding to a fourth focal length, the fourth focal length being different from the first focal length and the second focal length and the third focal length; and wherein the diffractive structure excludes a 0th diffractive order.

2. The multifocal ophthalmic lens of claim 1 wherein a chromatic aberration is reduced such that a polychromatic performance is substantially equivalent to a principle monochromatic performance.

3. The multifocal ophthalmic lens of claim 1 wherein the lens has at least one base curvature.

4. The multifocal ophthalmic lens of claim 1 wherein the at least one diffractive structure is incorporated into the anterior surface.

5. The multifocal ophthalmic lens of claim 1 wherein the at least one diffractive structure is incorporated into the posterior surface.

6. The multifocal ophthalmic lens of claim 1 further including at least a base curvature, a toricity, an asphericity, the at least one diffractive structure being a partial aperture diffractive structure and an apodization of the plurality of echelettes.

7. The multifocal ophthalmic lens of claim 1 wherein the ophthalmic lens is selected from an intraocular lens, a contact lens and a spectacle lens.

8. A multifocal ophthalmic device comprising:
an anterior surface, a posterior surface, and at least one diffractive structure including a plurality of echelettes having at least three different step heights of at least one wavelength and not more than two wavelengths in optical path length, the at least one diffractive structure residing on at least one of the anterior surface and the posterior surface, the at least one diffractive structure providing:
a first diffractive order for a first focus corresponding to a first focal length,
a second diffractive order for a second focus corresponding to a second focal length, the second focal length being different from the first focal length;
a third diffractive order for a third focus corresponding to a third focal length, the third focal length being different from the first focal length and the second focal length;
a fourth diffractive order for a fourth focus corresponding to a fourth focal length, the fourth focal length being different from the first focal length and the second focal length and the third focal length; and
wherein the diffractive structure excludes a 0th diffractive order; and
a plurality of haptics coupled with the ophthalmic lens.

9. The multifocal ophthalmic device of claim 8 wherein the ophthalmic lens has a fourth focus corresponding to at least a fourth focal length, the fourth focal length being different from the first focal length, and the second focal length, and the third focal length.

10. A method for fabricating a multifocal ophthalmic lens comprising:
designing an ophthalmic lens configured for use based upon a wavelength, the ophthalmic lens including an anterior surface, a posterior surface, and at least one diffractive structure including a plurality of echelettes having at least three different initial step heights, the at least one diffractive structure residing on at least one of the anterior surface and the posterior surface, the at least one diffractive structure providing
a first diffractive order for a first focus corresponding to a first focal length;
a second diffractive order for a second focus corresponding to a second focal length, the second focal length being different from the first focal length;
a third diffractive order for a third focus corresponding to a third focal length, the third focal length being different from the first focal length and the second focal length;
a fourth diffractive order for a fourth focus corresponding to a fourth focal length, the fourth focal length being different from the first focal length and the second focal length and the third focal length; and
wherein the diffractive structure excludes a 0th diffractive order;
adding one wavelength to the at least three initial step heights to provide at least three final step heights; and
fabricating the ophthalmic lens using the at least three final step heights for the at least one diffractive structure.

* * * * *